(12) United States Patent
Deitch

(10) Patent No.: US 9,717,490 B2
(45) Date of Patent: Aug. 1, 2017

(54) KIT OF PARTS FOR SURGICAL ANCHOR PLACEMENT, METHOD FOR PREPARING THE KIT OF PARTS AND A METHOD FOR SURGICAL ANCHOR PLACEMENT

(71) Applicant: Coloplast A/S, Humlebaek (DK)

(72) Inventor: Sarah J. Deitch, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 89 days.

(21) Appl. No.: 14/172,997

(22) Filed: Feb. 5, 2014

(65) Prior Publication Data

US 2015/0216521 A1 Aug. 6, 2015

(51) Int. Cl.
*A61B 17/064* (2006.01)
*A61B 17/04* (2006.01)

(52) U.S. Cl.
CPC ........ *A61B 17/0401* (2013.01); *A61B 17/064* (2013.01); *A61B 2017/0403* (2013.01); *A61B 2017/0412* (2013.01); *A61B 2017/0427* (2013.01); *A61B 2017/0445* (2013.01); *A61B 2017/0464* (2013.01); *A61B 2017/0647* (2013.01)

(58) Field of Classification Search
CPC .... A61B 17/04–2017/0649; A61F 2002/0823; A61F 2002/0841; A61F 2002/0858; A61F 2002/0829; A61F 2/08
USPC .......... 606/232, 139, 228–231, 104
See application file for complete search history.

(56) References Cited

U.S. PATENT DOCUMENTS

| | | | | |
|---|---|---|---|---|
| 5,957,953 | A * | 9/1999 | DiPoto | A61B 17/0401 606/232 |
| 6,632,245 | B2 * | 10/2003 | Kim | A61F 2/0811 606/232 |
| 7,588,587 | B2 * | 9/2009 | Barbieri | A61B 17/0401 606/232 |
| 2004/0138683 | A1 | 7/2004 | Shelton | |
| 2004/0204723 | A1* | 10/2004 | Kayan | A61B 17/064 606/151 |
| 2005/0278023 | A1* | 12/2005 | Zwirkoski | A61B 17/7094 623/11.11 |
| 2010/0198258 | A1* | 8/2010 | Heaven | A61B 17/0401 606/232 |

(Continued)

FOREIGN PATENT DOCUMENTS

DE 10300787 A1 9/2004
WO 2013046115 A1 4/2013

*Primary Examiner* — Kathleen Holwerda
*Assistant Examiner* — Socrates L Boutsikaris
(74) *Attorney, Agent, or Firm* — Coloplast Corp., Coloplast A/S; Nick Baumann

(57) ABSTRACT

Disclosed is a tissue anchor system and a kit of parts for surgical anchor placement including a needle having a length of suture attached to a trailing end of the needle. An opposite second end of the suture is provided with a stopper. The kit of parts further includes a plurality of surgical anchors each including an anchor body having a through-going lumen extending from a first opening in a proximal end to a second opening in a distal end. Each of the anchors is provided on the length of suture between the first and the second ends of the suture. Also disclosed is a method of preparing a kit of parts and a method of attaching a surgical implant inside the body of a patient.

17 Claims, 17 Drawing Sheets

(56) References Cited

U.S. PATENT DOCUMENTS

2011/0190815 A1* 8/2011 Saliman ............ A61B 17/0401
606/232

* cited by examiner

KIT OF PARTS FOR SURGICAL ANCHOR PLACEMENT, METHOD FOR PREPARING THE KIT OF PARTS AND A METHOD FOR SURGICAL ANCHOR PLACEMENT

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon is unable to see the suture site. In such a case, the surgeon will digitally palpate with a finger to locate a landmark within the intracorporeal site, and then deliver the suture at or near the landmark. Tying of the suture inside the patient at the intracorporeal site can be challenging since the surgeon is unable to see the site.

Improved suturing instruments and improved methods of delivering sutures would be welcomed by the surgical staff.

SUMMARY

One aspect provides a tissue anchor system that includes a suture attached to a needle and a set of nestable anchors suspended on the suture. The nestable anchors each include a shaft defining a through-going lumen, the shaft of one anchor being insertable into and adapted to nest in the lumen of the shaft of a neighbouring anchor. The shaft of each nestable anchor includes an outer surface whereon a plurality of barbs is provided. The outer surface of the shaft of the anchor is further tapered from a proximal end to a distal end such that the distal end is narrower than the proximal end. The system is useful for delivering the plurality of anchors to different tissue locations inside a patient's body one at a time such as in order to attach a surgical implant at the different target tissue locations. Since the anchors are nestable within each other the system takes up less space in the patient's body and the surgeon does not need to externalize the needle to load a new anchor onto the suture.

One aspect provides a kit of parts for surgical anchor placement including a needle having a length of suture attached to a trailing end of the needle. An opposite second end of the suture is provided with a stopper. The kit of parts further includes a plurality of surgical anchors each including an anchor body having a through-going lumen extending from a first opening in a proximal end to a second opening in a distal end. Each of the anchors is provided on the length of suture between the first and the second ends of the suture.

One aspect provides a method of preparing a kit of parts for surgical anchor placement that includes providing a needle with a length of suture attached thereto and providing a stopper at a second end of the suture and receiving a plurality of surgical anchors on the length of suture.

One aspect provides a method of attaching a surgical implant inside the body of a patient using a kit of parts for surgical anchor placement.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The individual figures and elements of the figures are not necessarily to scale relative to each other. Like reference numerals designate corresponding similar parts.

DETAILED DESCRIPTION

Figure 1:
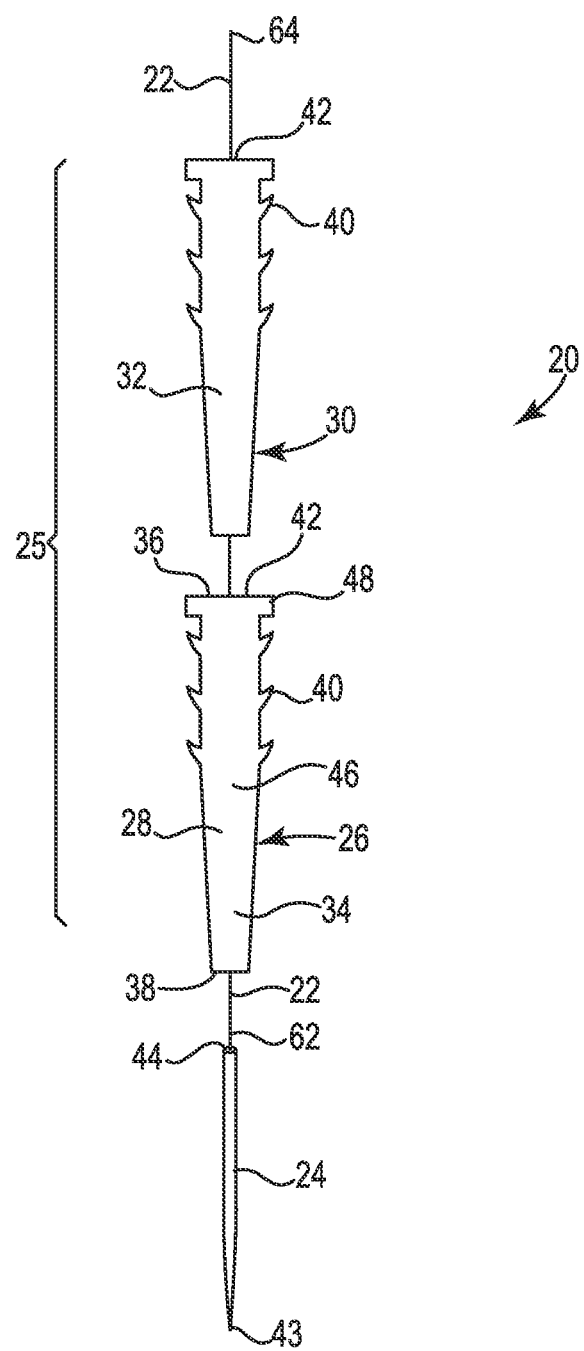
FIG. 1 is a side view of one embodiment of a tissue anchor system.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Anterior means "forward" or "front," and posterior means "rearward" or "back." Relative to surfaces of an organ in the human body, an anterior surface is oriented forward toward the belly and a posterior surface is oriented rearward toward the spine.

The term "distal" as employed in this application means that part that is located farthest away from the person introducing the system or kit during insertion through an incision in the body. The term "proximal" as employed in this application means that part that is located closest to the person introducing the system or kit during insertion through an incision in the body. A distal end is the furthest endmost location of a distal portion of a thing being described, whereas a proximal end is the nearest endmost location of a proximal portion of the thing being described.

The term "plurality" as employed in this application means at least two, i.e. including a minimum of two and up to any number of the thing being described, but excluding one or a single specimen of the thing being described.

Embodiments provide a tissue anchor system including a suture attached to a needle and several surgical anchors secured in a sliding on/off arrangement with the suture. The system is useful for delivering each of the anchors to different tissue locations inside a patient's body. One useful application of the system allows a surgeon to attach a surgical implant by placing individual anchors sequentially at different tissue locations without removing the needle from the patient to load a new anchor onto the suture. For example, during a laparoscopic procedure, the system allows the surgeon to "tack down" one area of a support or implant inside the patient with a first anchor, and subsequently allows the surgeon to fully secure the support/implant with additional anchors without having to withdraw the needle/suture from the laparoscopic space. The system improves efficiency of surgical procedures, including laparoscopic procedures and robotically assisted surgical procedures.

The surgical anchors each include a shaft extending from a proximal end to a distal end defining a lumen. The shaft of the anchor has an outer surface that tapers from the proximal end to the distal end so that the distal end of the shaft is narrower than the proximal end. The outer surface of the shaft includes a plurality of barbs for securing the surgical anchor in tissue. The plurality of barbs is located distal to the proximal end. In use of the system, the plurality, or set, of surgical anchors is suspended by the suture that is attached to the needle at a trailing end of the needle, the suture extending through the lumen of each of the surgical anchors. The shaft of one surgical anchor is insertable into and adapted to nest in the shaft of another surgical anchor. By nesting a surgical anchor within a neighbouring anchor, a tissue anchor system is provided that takes up less space and is less bulky and in addition requires only one needle to keep track of all surgical anchors necessary for the attachment of a particular surgical implant. Suspending the plurality of anchors in this nested manner on the suture additionally facilitates use of a surgical robot for performing part, or all, of the surgical procedure, which in turn saves both time and money.

FIG. 1 is a side view of one embodiment of a tissue anchor system 20. The system 20 includes a suture 22 attached to a needle 24 and a set 25 of nested anchors including a first anchor 26 having a first shaft 28 and a second anchor 30 having a second shaft 32. The set 25 can include two or more anchors. One useful set 25 includes four anchors 26, although a set 25 of ten or more anchors is within the scope of this disclosure. Each of the first shaft 28 and the second shaft 32 has an outer surface 34 that tapers from a proximal end 36 to a distal end 38 that is narrower than the proximal end 36. Each of the shafts 28 and 32 has a lumen 42 extending from the proximal end 36 to the distal end 38. The lumen 42 provides a passage through the anchor 26 from the proximal end 36 to the distal end 38 and vice versa. The outer surface 34 of each of the first shaft 28 and the second shaft 32 includes a plurality of barbs 40 located distal the proximal end 36. The needle 24 includes a trailing end 44 to which the suture 22 attaches and the plurality of anchors 26, 28 are suspended by (or on) the suture 22, the suture 22 extending through the lumen 42 of the first and the second shafts 28, 32.

Figure 1A:
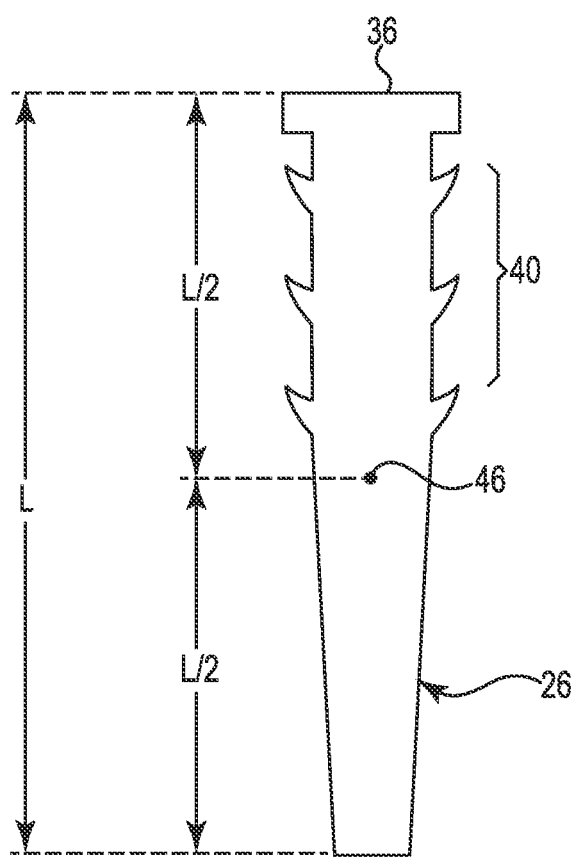
FIG. 1A is a side view of one embodiment of an anchor with one distribution of retaining elements in relation to proportions of the anchor.

An outer surface 34 of the shafts includes a plurality of barbs or other suitable retaining elements 40 that are provided to retain the anchors in place once inserted in a target tissue location. The barbs or retaining elements 40 are configured with a pointy end directed towards the proximal end 36 of the anchors, but other suitable configurations of the barbs 40 are acceptable. In embodiments, the plurality of barbs 40 are located between a shaft mid-point 46 and the proximal end 36 (FIG. 1A). In embodiments, the outer surface 34 of the first and second shafts 28,32 is smooth and has no barbs or retaining elements 40 provided between the shaft mid-point 46 and the distal end 38. Other suitable distributions of the plurality of barbs or retaining elements 40 are acceptable, including embodiments configured with a minority of barbs between the shaft mid-point and the distal end and a majority of barbs between the shaft mid-point and the proximal end. In embodiments, barbs or retaining elements located between the shaft mid-point and the distal end have a different size or shape than barbs or retaining elements located between the shaft mid-point and the proximal end.

The outer surface 34 of the shafts 28,32 tapers from the proximal end 36 to the distal end 38 such that the distal end 38 of the shaft is narrower than the proximal end 36. This configuration of the anchors reduces the force needed to deliver an anchor into a target tissue location and further provides a set of anchors where a first anchor will nest or stack in the shaft of a neighbouring anchor, and the first anchor will receive a third anchor that will nest or stack in the lumen of the first anchor.

In embodiments the anchors 26, 30 include a flange 48 provided at the proximal end 36. The flange 48 extends radially outward from the shaft 28,32 of the anchor and is provided annually around a first opening 50 (as better seen in FIG. 4) into the lumen 42 at the proximal end 36. Together with the outer surface 34 or the shaft 28,32 the flange 48 is useful for providing a stop or abutment for a surgical implant, such as, but not limited to, a polypropylene mesh used in pelvic floor repair surgery.

Figure 2:
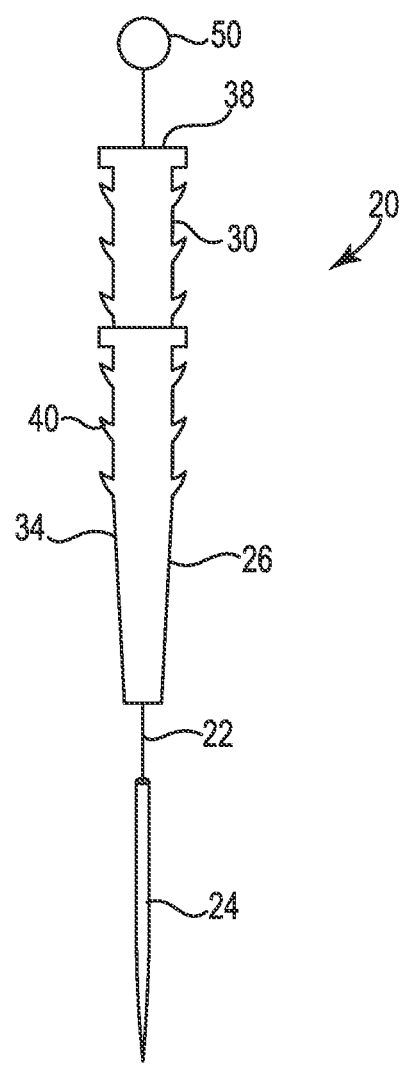
FIG. 2 is a side view of one embodiment of a tissue anchor system including a set of nested anchors.

FIG. 2 is a side view of one embodiment wherein the second shaft 32 of the second anchor 30 is nested in the first shaft 28 of the first anchor 26. In the embodiment shown, the set of nested anchors includes two anchors 26 and 30. In other embodiments the set of nested anchors includes any number of anchors required in a specific surgical procedure.

FIG. 2 is a side view of one embodiment wherein the system 20 includes a holding element such as a stopper 50 at a trailing end of the suture 22 for holding or abutting the proximal end of a proximal-most anchor, such as proximal end 38 of second anchor 30. In FIG. 2, the stopper 50 includes a ball or sphere shaped configuration. In embodiments a trailing end (not shown) of the suture 22 is attached inside the stopper 50. In other embodiments, the suture 22 passes through a suture passage in the stopper 50 and extends to a position outside the stopper 50. In embodiments, the stopper 50 includes a manipulable suture engagement mechanism configured to allow the stopper 50 to be moved along the suture 22 when the mechanism is engaged and to arrest the stopper 50 on the suture 22 when the mechanism is in a resting position. This facilitates adjustment of the available length of suture 22 onto which anchors are suspended. Thereby, in embodiments, the system 20 can be configured to include a larger or smaller number of nested anchors, also depending on the length of the suture 22. In other embodiments, the holding element includes other suitable stoppers, also including non-movable stoppers such as a simple surgeon's knot.

Figure 3:
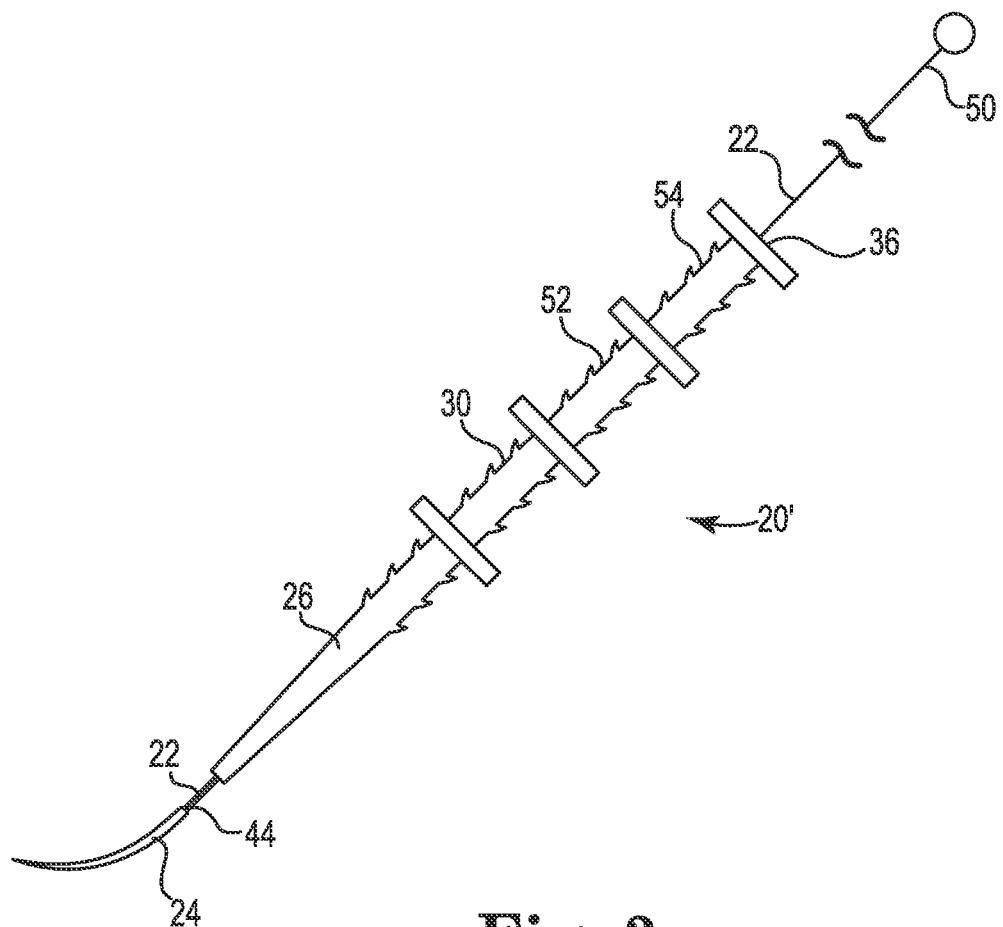
FIG. 3 is another side view of one embodiment of a tissue anchor system including a set of nested anchors.

FIG. 3 is a side view of one embodiment of a system 20' including a set of four anchors 26, 30, 52, 54 of which three (30, 52, 54) are nested in the immediate neighbouring anchor. Proximal-most anchor 54 abuts stopper 50 at the proximal end 36 of the anchor. The set of nested anchors is suspended on suture 22 extending from trailing end 44 of needle 24. The needle 24 is shown as a surgical needle, by way of example having a curved configuration suited for intracorporeal suturing procedures.

Figure 4:
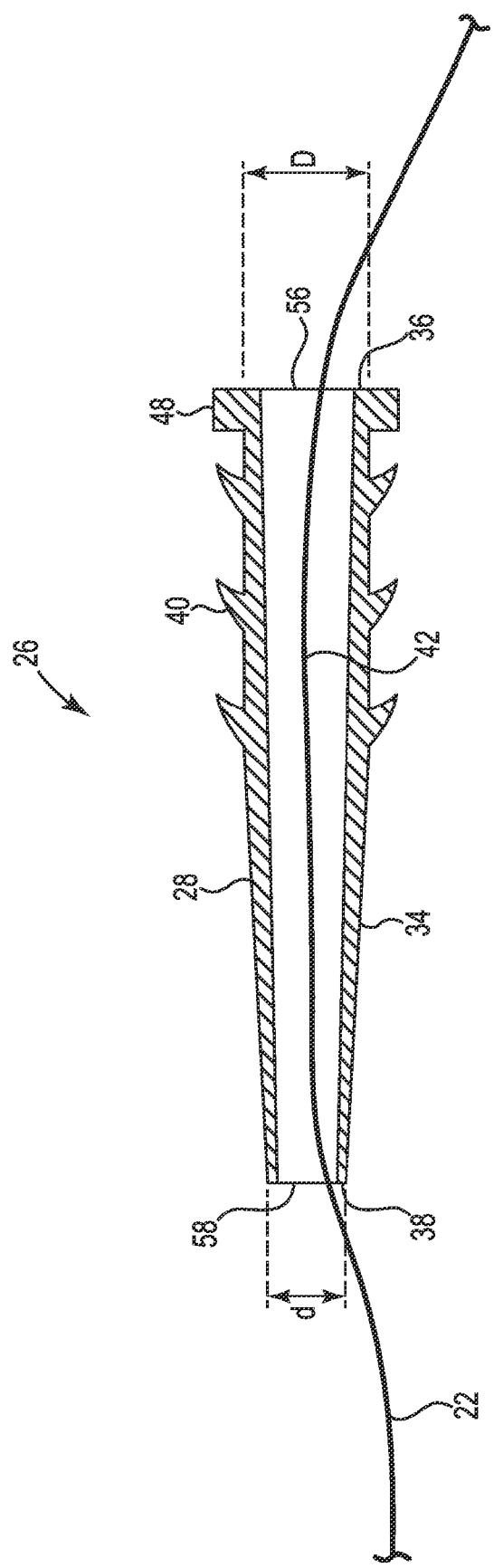
FIG. 4 is a cross-sectional view of one embodiment of a surgical anchor.

FIG. 4 is a cross-sectional side view of one anchor, such as first anchor 26, showing the internal lumen 42 extending through the anchor from the proximal end 36 to the distal end 38. The outer surface 34 of the shaft tapers from the proximal end 36 to the distal end 38 such that a second diameter d of second opening 58 at the distal end 38 of anchor 26 is smaller than a first diameter D of first opening 56 at the proximal end 36 or, in other words, that the distal end 38 is narrower than the proximal end 36 of the anchor 26. The tapering outer surface 34 of the shaft 28 eases insertion of the surgical anchor into a target tissue location. It also facilitates the nesting of the anchor into the lumen 42 of a neighbouring anchor. The anchor 22 is suspended on suture 22 that extends through the lumen 42 of the anchor.

In embodiments, the surgical anchors include one or more polymeric material components. In embodiments, the anchors are configured to have a high degree of flexibility, at least in a transverse direction to the longitudinal extent of the shaft of the anchor. This provides for the anchors to be flexed, i.e. also when a plurality of anchors are nested within each other, such as to be able to bend in the often narrow operating space in the patient's body and to be able to flex according to a possible curved configuration of the needle. In embodiments, the anchors include one or more bioabsorbable materials. The anchors may be fabricated from suitable bioabsorbable materials such as biodegradable polymers, for example, polylactide, polyglycolide, poly(lactide-co-glycolide), or polylactic acid-based polymers. These bio-absorbable materials are suitably formed into anchors by molding, pressing, injection molding and other three-dimensional solid forming processes.

Figure 5:
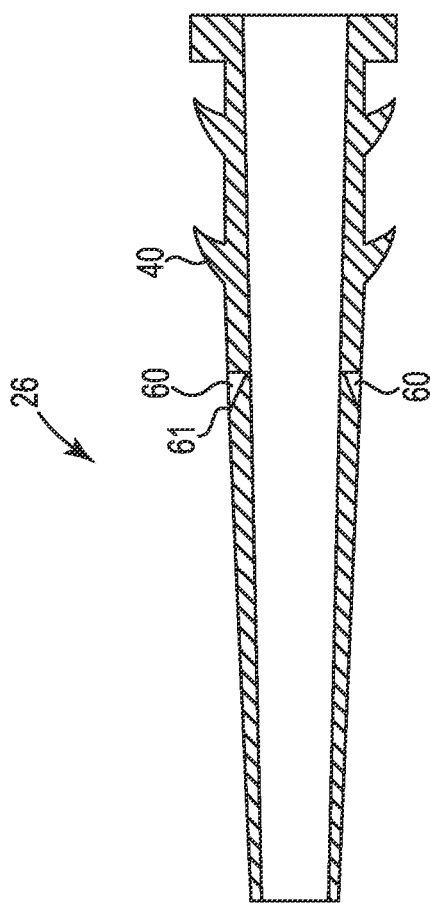
FIG. 5 is a cross-sectional view of one embodiment of a surgical anchor including a hinged barb.
Figure 5A:
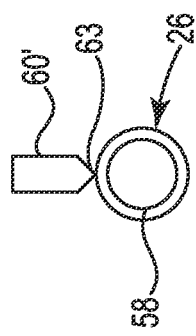
FIG. 5A is a cross-sectional end view of one embodiment of a surgical anchor including a living hinge.

FIG. 5 is a schematic cross-sectional view of one embodiment wherein one or more of the barbs or retaining elements 40 include, or configure to form, a hinged barb or retaining element 60 so as to enable the barb or retaining element to be moved toward a central longitudinal axis of the shaft 28 to make the barb substantially flush with the outer surface 34 of the shaft 28, at least when the anchor 26 is forced through tissue. The hinged barb 60 should be configured with sufficient resiliency to be able to return to an elevated position over the outer surface of the shaft when it is not exerted to any outside force. In one embodiment, the hinged barb 60 configures as a biased barb turning around pivot point 61. In one embodiment, the hinged barb includes a living hinge (FIG. 5A). In one embodiment, the living hinge forms as a thin flexible hinge 63 made from the same material as the anchor 26 being thinned or cut along a bend line or point. The hinged barb configuration enables a system having anchors that can be nested further into the lumen of a neighbouring anchor to thereby compact a set of nested anchors even more e.g. during storage, during entry through an incision into the patient's body and/or during penetration through tissue at a desired location.

In an aspect, the application relates to a kit of parts for surgical anchor placement.

Figure 6:
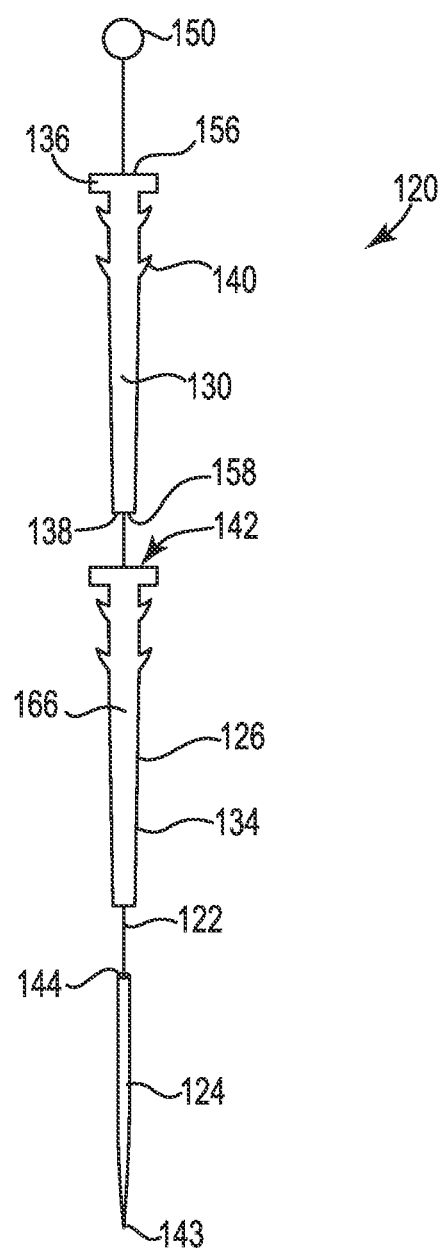
FIG. 6 is a side view of one embodiment of a kit of parts for surgical anchor placement.

FIG. 6 is a schematic side view of one embodiment providing a kit of parts 120 for surgical anchor placement. The kit of parts 120 includes a needle 124 having a front end 143 and a trailing end 144 and a length of suture 122 having a first end 162 attached to the trailing end 144 of the needle 124 and a second end 164 provided with a stopper 150. The kit of parts also includes a plurality of surgical anchors 126,130. Each of the anchors 126,130 include an anchor body 166 having a through-going lumen 142, or passage, extending longitudinally through the anchor body 166 from a first opening 156 in a proximal end 136 to a second opening 158 in a distal end 138. The anchor body 166 has an outer surface 134 that includes a plurality of retaining elements 140 located on the outer surface. Each of the plurality of anchors 126,130 is provided on the length of suture 122 between the first 162 and the second 164 ends of the suture 122. The suture 122 extends through the lumen 142 in each of the anchors 126,130.

Figure 7:
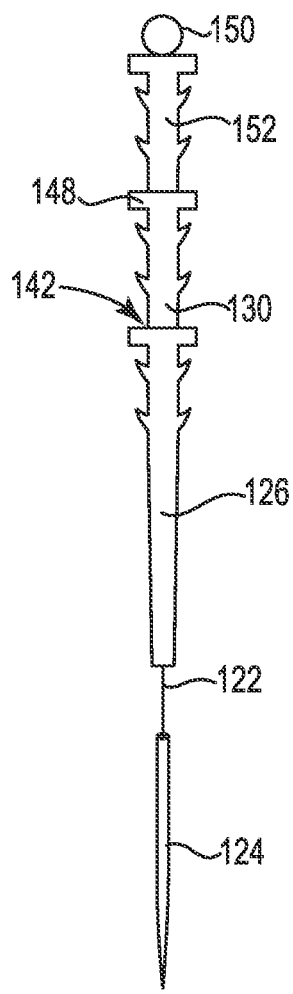
FIG. 7 is another side view of one embodiment of a kit of parts for surgical anchor placement including a set of nested anchors.

FIG. 7 shows one embodiment, wherein each of the plurality of anchors 126, 130, 152 is configured to be nesting in or on another anchor. At least a portion of the anchor body 166 of an anchor is adapted to be insertable into the lumen 142 of another anchor. Alternative configurations of the outer surface 134 of the anchors are acceptable, such as, but not limited to the tapering configuration as detailed above with respect to the tissue anchor system.

Figure 8:
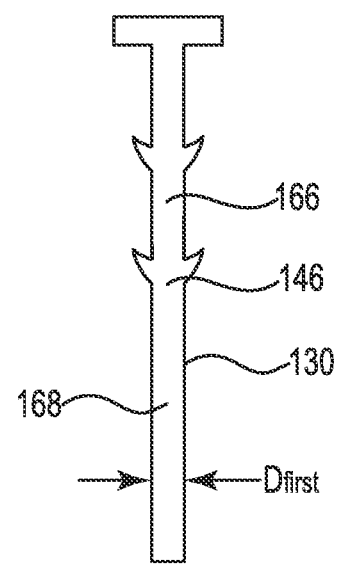
FIG. 8 is an enlarged side view of a set of nestable anchors.
Figure 8:
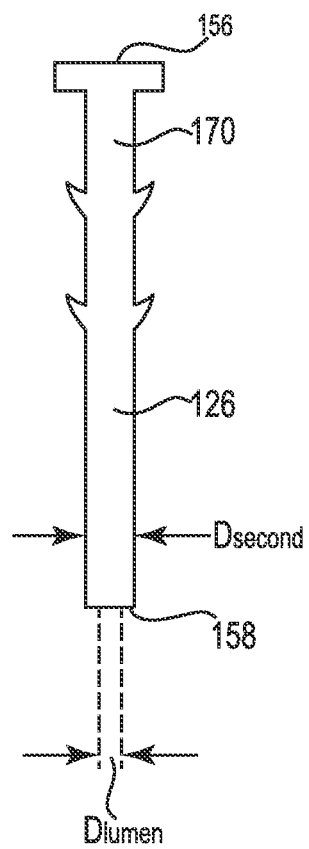

FIG. 8 shows one embodiment wherein the anchors have anchor bodies of different diameter such that a first anchor 130 with an anchor body 166 having a slightly reduced outer diameter D(first) compared to both an outer diameter D(second) and an inner diameter of the lumen D(lumen) of a second anchor 126 in which the first anchor 130 nests, is easily slid in and out of nesting engagement with the second anchor 126. In embodiments, a distal end portion 168 of the anchor body 166 extends into a proximal end portion 170 of another anchor body. Some embodiments include a flange 148 at the proximal end 136 of the anchor body 166 as well as first and second openings 156 and 158 at the proximal and distal ends 136, 138 of the anchor body 166 similarly to those described with respect to the tissue anchor system above. In some embodiments, the portion of an anchor nesting inside the through-going lumen of another anchor is the portion of the anchor body 166 extending between the distal end 138 and an anchor body mid-point 146. Other suitable distributions of the nesting portions are acceptable.

Figure 9:
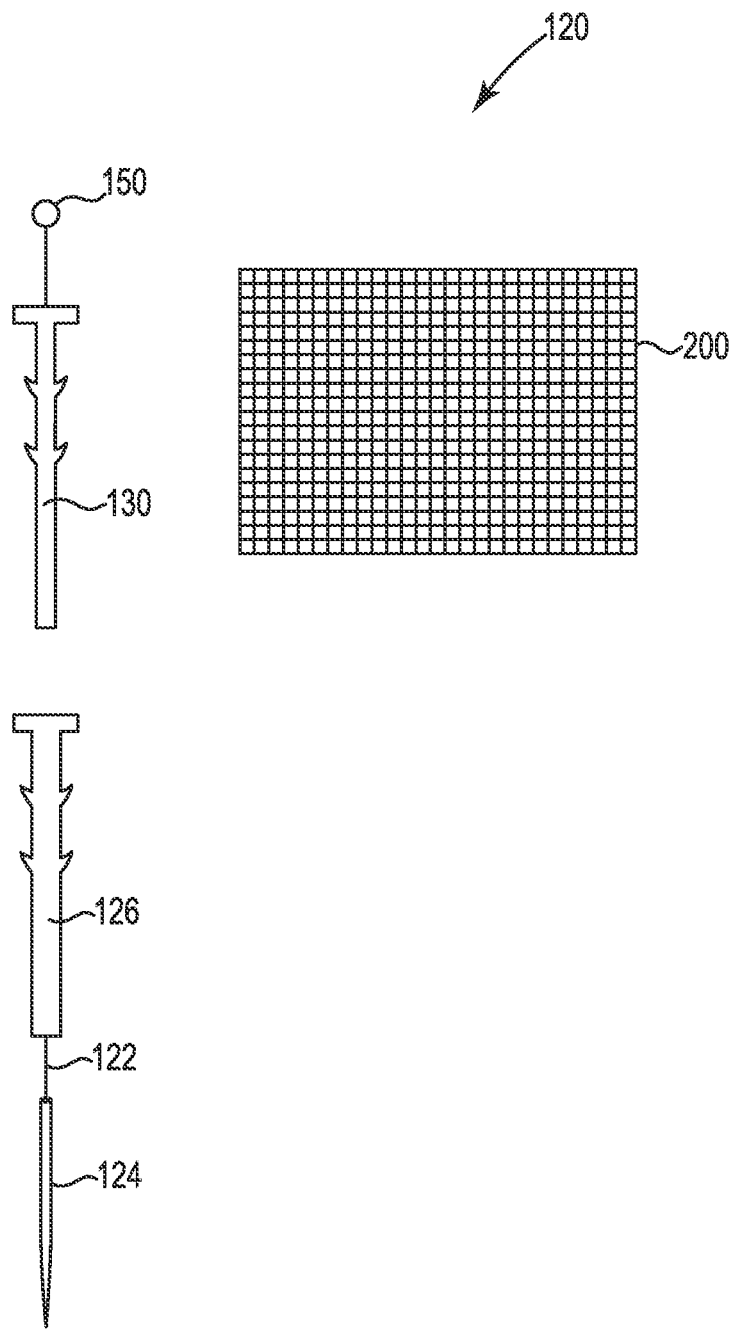
FIG. 9 is a schematic side view of a kit of parts for surgical anchor placement including a surgical implant.

FIG. 9 shows one embodiment wherein the kit of parts 120 further includes a surgical implant 200. Suitable materials for fabricating the surgical implant 200 include porous materials that allow tissue ingrowth throughout the implant structure to anchor the implant 200 in the body after implantation and healing. Suitable such porous materials include autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the support 200. The pores are generally larger, on average, than 75 µm.

Figure 10:
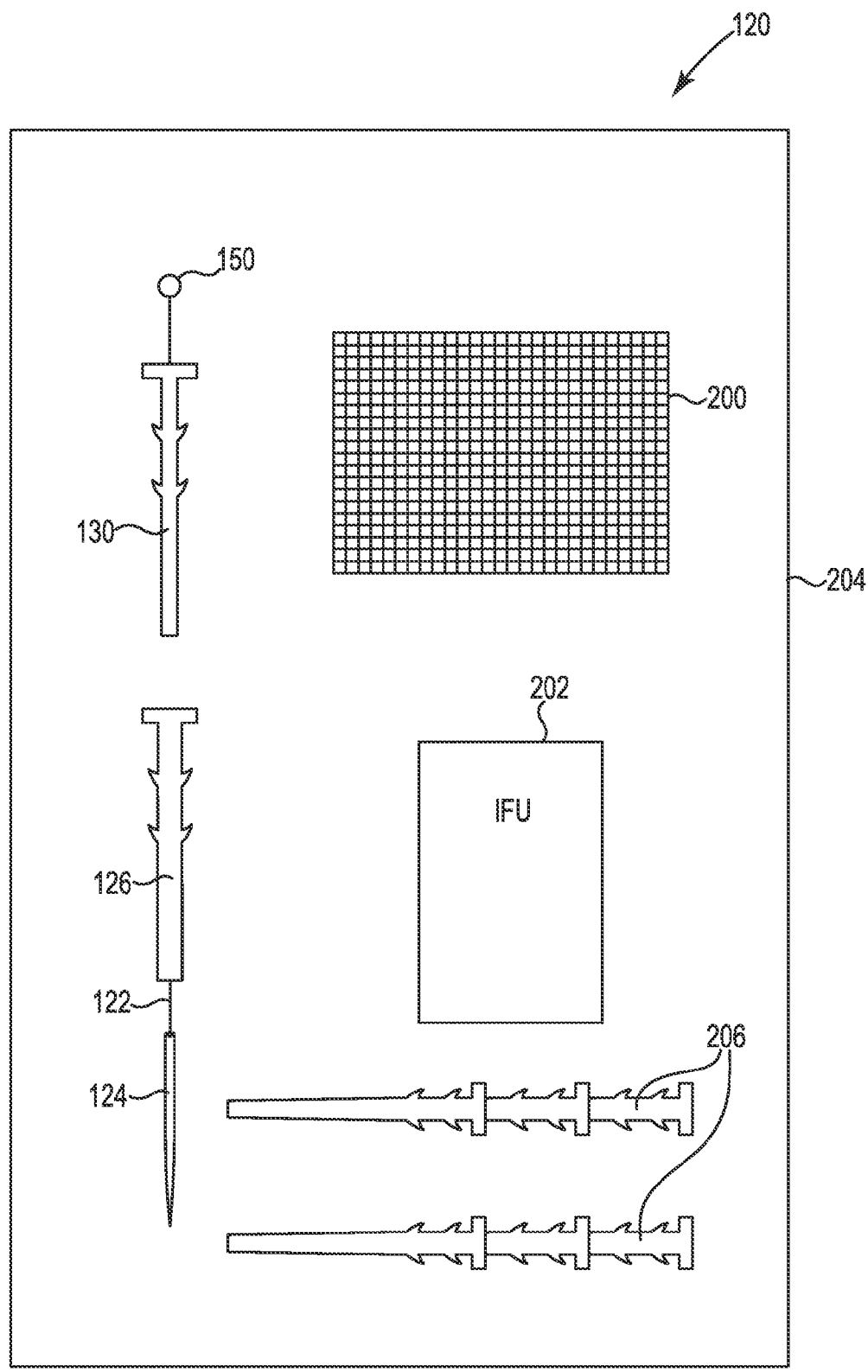
FIG. 10 is a schematic top view of a kit of parts for surgical anchor placement including a surgical implant and a set of instructions for use.

FIG. 10 shows one embodiment wherein a kit of parts 220 includes a needle 124 and a length of suture 122 having a second end provided with a stopper 150. The kit of parts also includes a plurality of surgical anchors 126,130 provided on the suture 122, a surgical implant 200 and a set of instructions for use 202. The kit includes and is provided in a packaging 204. In embodiments, the kit of parts further includes additional anchors 206 that can be added to the anchors 126,130 already provided on the suture 122. In FIG. 10, six additional anchors 206 are shown, but any number of anchors is acceptable.

In an aspect, the application relates to a method of preparing a kit of parts for surgical anchor placement.

Figure 11:
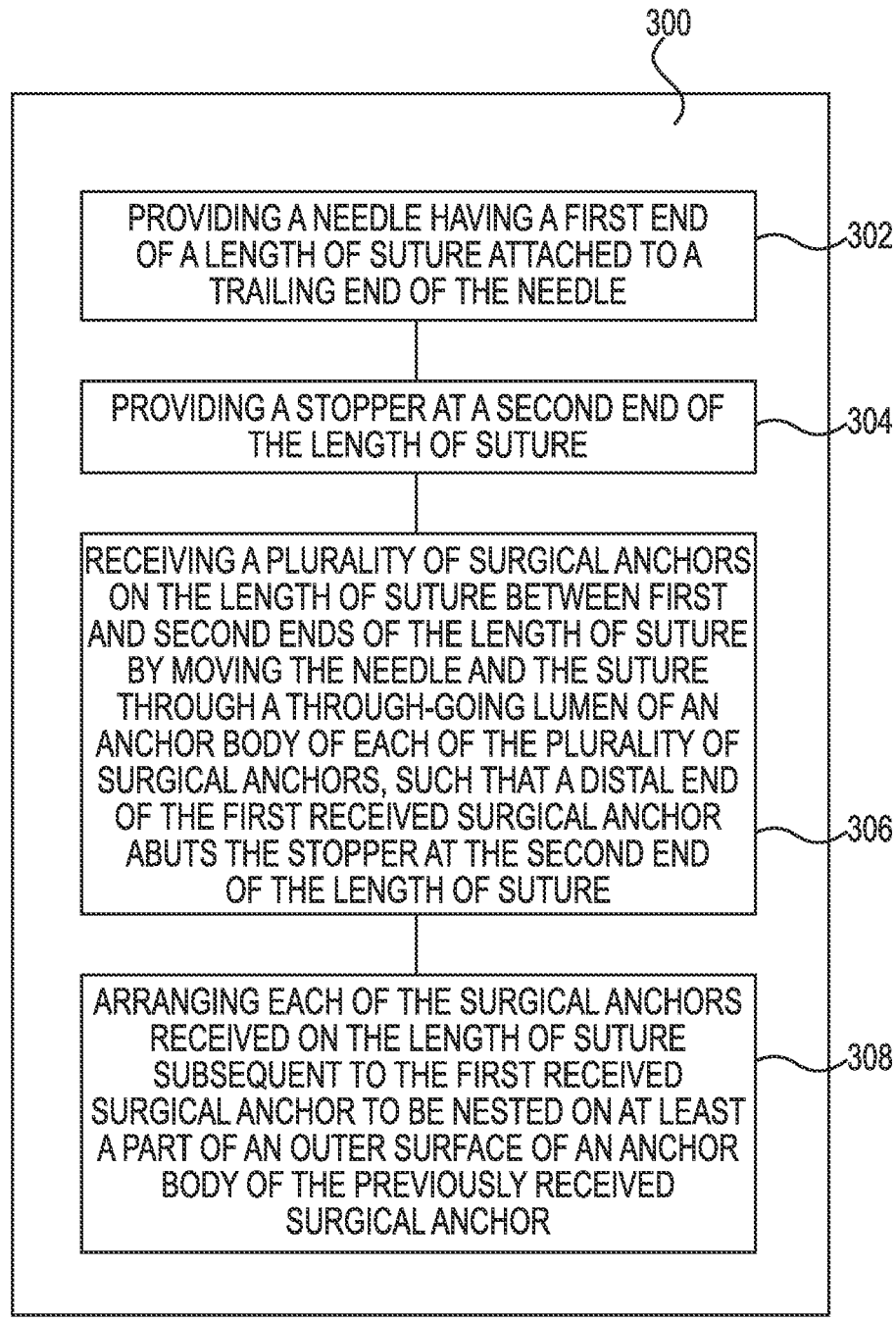
FIG. 11 is a block diagram of one embodiment of a method of preparing a kit of parts for surgical anchor placement.

FIG. 11 is a block diagram 300 of one embodiment of a method of preparing a kit of parts for surgical anchor placement. The method includes at 302 providing a needle having a first end of a length of suture attached to a trailing end of the needle. The method includes at 304 providing a stopper at a second end of the length of suture. The method includes at 306 receiving a plurality of surgical anchors on the length of suture between first and second ends of the length of suture by moving, such as by pulling, the needle and the suture through a through-going lumen of an anchor body of each of the plurality of surgical anchors, such that a distal end of the first received surgical anchor abuts the stopper at the second end of the length of suture.

Thereby, the kit of parts is prepared for a surgical procedure in which surgical anchors are to be delivered into a target tissue location inside a patient's body.

In one embodiment, the method includes at 308 arranging each of the surgical anchors received on the length of suture subsequent to the first received surgical anchor to be nested on at least a part of an outer surface of an anchor body of the previously received surgical anchor. Thereby, the plurality of surgical anchors are provided in a nesting relationship with each other taking up less space in the often narrow operating space in the patient's body available to the surgeon during a surgical procedure. Also, providing all of the anchors (indicated for a given procedure) on a suture attached to a single needle reduces the number of surgical instruments in the field of the procedure and also reduces the number of entries and exits through the surgical incision to the benefit of the patient. The system thus improves inventory control.

Figure 12:
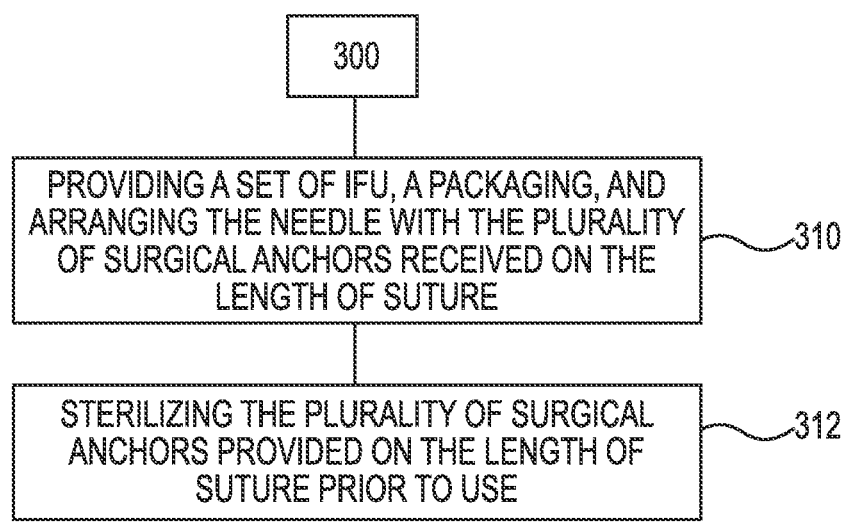
FIG. 12 is a block diagram of another embodiment of a method of preparing a kit of parts for surgical anchor placement.

FIG. 12 is a block diagram showing one embodiment, wherein the method for preparing a kit of parts at 310 further includes providing a set of instructions for use (in the following designated as IFU), providing a packaging 204 and arranging the needle with the plurality of surgical anchors received on the length of suture and the IFU in the packaging 204.

The IFU includes instructions and directions to guide the surgeon on how to use the kit of parts. The instructions include the following: initially, the packaging 204 is opened so that every element of the kit of parts, such as kit of parts 220 (FIG. 10) is easily accessible to the surgeon. Next, depending on the number of anchors needed for the procedure to be performed, the needle 124 and the length of suture 122 is threaded through the lumens of the desired number of surgical anchors. It is made sure that the surgical anchors nest inside each other as is necessary for the procedure. The needle and anchors are entered through the incision. The needle 124 is driven through a first designated part of the surgical implant 200 and pulled so that a first anchor engages with the implant (alternatively this is done outside the patient's body before entering through the incision). A desired anchor location is determined by the surgeon. The needle 124 is driven through the tissue location and pulled until the barbs or retaining elements of the first anchor is secured to the tissue. The needle 124 is then withdrawn or retracted through the lumen of the) now secured) first anchor. The needle 124 is then driven through a next designated part of the surgical implant 200 to engage a second anchor with the implant. A next desired tissue location is identified. The needle 124 is driven through the next tissue location and pulled until the barbs or retaining elements of the second anchor is secured to the tissue. The needle 124 is then withdrawn or retracted through the lumen of the second anchor. These steps are repeated as often as required according to the number of anchors necessary for the procedure and/or until the surgical implant 200 is secured to the surgeon's satisfaction.

In one embodiment, at 312 the needle with the plurality of surgical anchors received on the length of suture is sterilized prior to use. In embodiments, a stopper is attached to a trailing end of the suture and also sterilized. In embodiments, the sterilization is carried out each of the elements of the kit of parts separately which are then subsequently arranged as the kit of parts. In other embodiments the sterilization is carried out on all the parts of the kit in one single operation. This may be performed with the kit of parts provided in the packaging before the sterilization such that it is in practice ready for use after the sterilization.

In an aspect, the application relates to a method of attaching a surgical implant inside the body of a patient.

Figure 13:
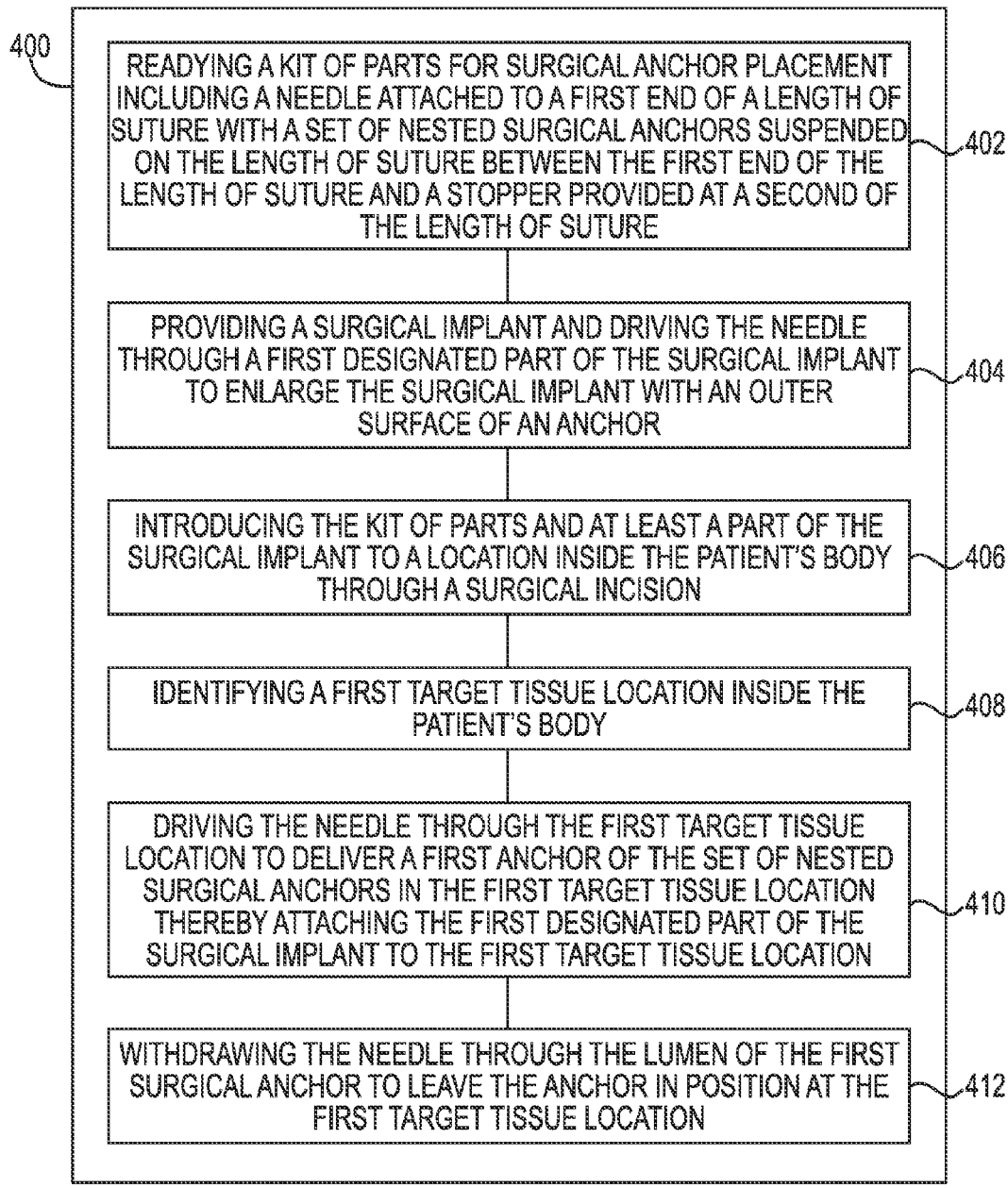
FIG. 13 is a block diagram of one embodiment of a method of attaching a surgical implant inside the body of a patient.

FIG. 13 is a block diagram showing one embodiment 400 of a method of attaching a surgical implant inside the body of a patient. At 402 the method includes readying a kit of parts, for example kit 120, for surgical anchor placement including a needle attached to a first end of suture with a set of nested surgical anchors suspended on the length of suture between the first end of the length of suture and a stopper provided at a second end of the length of suture. At 404 the method includes providing a surgical implant and driving the needle through a first designated part of the surgical implant to engage the surgical implant with an outer surface of an anchor. At 406 the method includes introducing the kit of parts 120 and at least a part of the surgical implant to a location inside the patient's body through a surgical incision. At 408 the method includes identifying a first target tissue location inside the patient's body. At 410 the method includes driving the needle through the first target tissue location to deliver a first anchor of the set of nested surgical anchors in the first target tissue location thereby attaching the relevant part of the surgical implant to the first target tissue location. At 412 the method includes withdrawing the needle through the lumen of the first surgical anchor to the leave the anchor in position at the first target tissue location.

Thereby, the method provides for attachment of a surgical implant to multiple designated target locations inside a patient's body without having to externalize the needle to load a new anchor onto the suture since the necessary anchors are nested within each other and takes up only little space in the operating area. This is further advantageous in surgical procedures wherein the procedure is performed through a single surgical incision.

Figure 14:
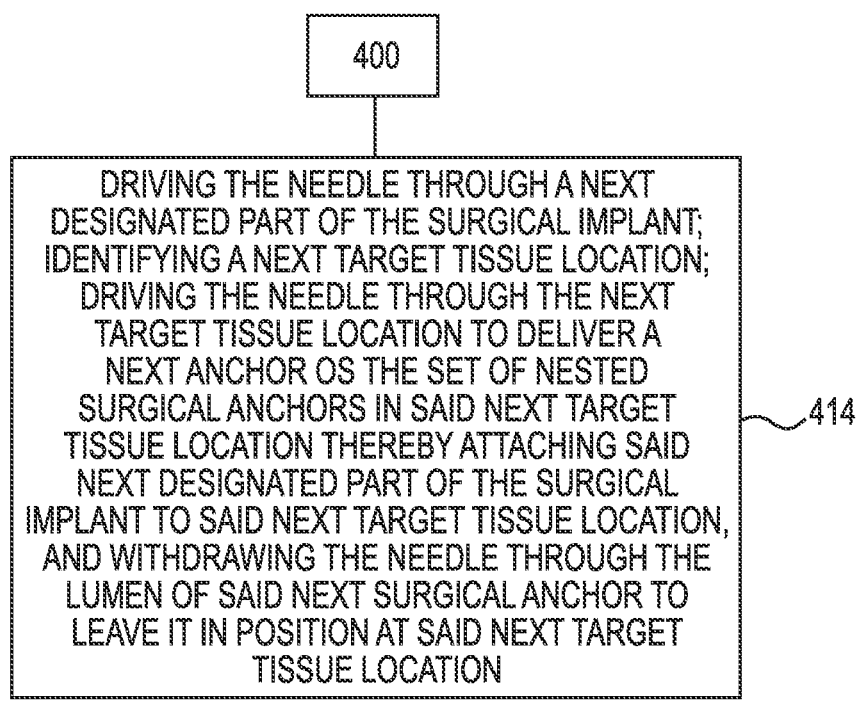
FIG. 14 is a block diagram of another embodiment of a method of attaching a surgical implant inside the body of a patient.

FIG. 14 shows one embodiment of the method for attachment of a surgical implant including driving the needle through a next designated part of the surgical implant; identifying a next target tissue location; driving the needle through the next target tissue location to deliver a next anchor of the set of nested surgical anchors in said next target tissue location thereby attaching said next designated part of the surgical implant to said next target tissue location, and withdrawing the needle through the lumen of said next surgical anchor to leave it in position at the said next target tissue location.

Figure 15:
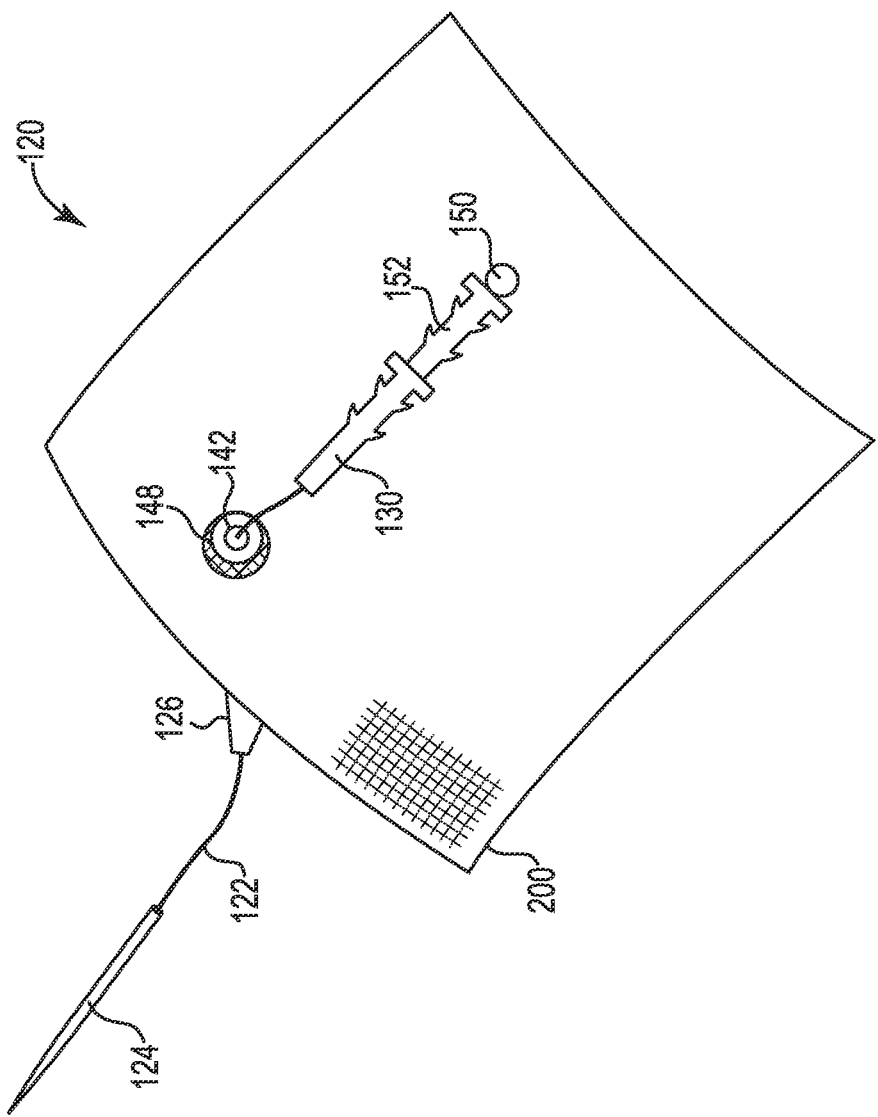
FIG. 15 is schematic perspective view of a kit of parts for surgical anchor placement with one surgical anchor driven through a surgical implant.
Figure 16:
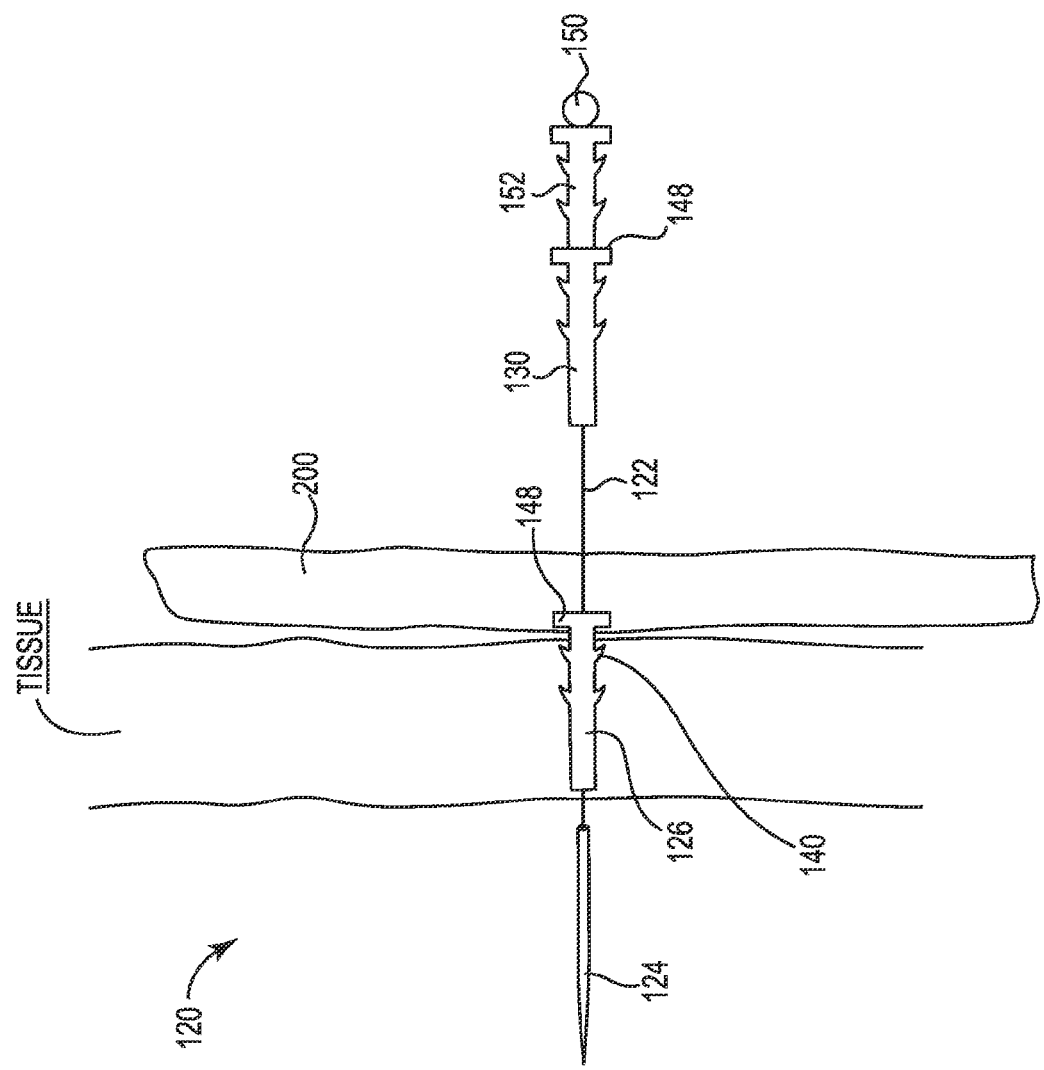
FIG. 16 is a schematic cross-sectional view of a kit of parts for surgical anchor placement with one surgical anchor driven through a surgical implant attached in a first target tissue location inside a patient's body.

With additional reference to FIGS. 15 and 16, which are a perspective view and a schematic side view, respectively, of a kit of parts for surgical anchor placement 120 is provided for attaching an anchor 126, 130, 152 to a designated target tissue location in a patient in an intracorporeal suturing procedure. A length of suture 122 is attached to the needle 124. The suture is configured to extend through a surgical implant 200 including a support material, the support material including a porous support or mesh type support material for supporting internal organs or tissues. The anchors 126, 130, 152 are useful for fixating the support material within the patient's body. The anchors 126, 130, 152 of the kit of parts 120 are nested within each other to provide a compact kit solution so that the surgeon can deploy the anchors 126, 130, 152 with a single needle through a single incision and into e.g. the periosteum tissue that covers the pubic bone or to a ligament, particularly including the sacrospinous and arcus tendenius ligaments.

Example

The following example illustrates, with particular reference to FIGS. 15-16, the method of attaching surgical anchors inside the body of a patient using the kit of parts described above.

The patient is prepared for the relevant type of surgery, such as, sacrocolpopexy surgery in a female patient. For the sacrocolpopexy procedure the patient is oriented in a Trendelenburg position with the patient's head generally at a lower elevation than the feet. For an open vaginal procedure, the patient is positioned on a surgical operating table in a lithotomy, or modified lithotomy position. Prior to both procedures the patient is anesthetized.

The surgeon makes an incision in the pelvic region of the patient. One acceptable incision approach is a single incision approach including the formation of a single (exactly one) incision in the anterior wall of the vagina (e.g., an upper wall of the vagina with the patient in the lithotomy position). Tissue is dissected lateral and distal the incision to access the supporting ligaments and other tissue in the pelvis.

The needle 124 with the length of suture 122 attached to the trailing end of the needle 124 is driven through the support material at a first designated part of the surgical implant 200 either prior to or subsequent to introducing the kit of parts 120 through the surgical incision. The needle 124 is driven into a target tissue location and pulled until surgical anchor 126 pass through the surgical implant 200 and is delivered into the target tissue location such that an outer surface 134 of the anchor 126, including the flange 148, contacts the implant 200 to secure a first designated part of the surgical implant 200 to the target tissue location.

When the first surgical anchor 126 has been secured in the first target tissue location, the needle 124 is withdrawn, or pulled backwards, through the lumen 142 of the first surgical anchor 126 leaving the first anchor 126 in place in the first target tissue location and separated from the kit of parts 120. The kit of parts 120 is then ready for delivering a next surgical anchor 130 in a next target tissue location and the needle 124 is driven through a next designated part of the surgical implant 200 and pulled until the next surgical anchor 130 pass through the surgical implant 200 and is delivered into the next target tissue location, attaching the surgical implant 200 in a manner as similar for the first anchor described above. In embodiments, the method of attaching the surgical implant includes attaching each necessary surgical anchor one at a time until the implant has been attached as required in the given surgical procedure.

In some implementations of the aspects of the invention, the surgical anchors are used for native tissue repair in pelvic organ floor prolapses. This includes joining or securing native tissues to each other, e.g. attaching prolapsed tissue to a ligament or similar by driving the needle and the surgical anchor through all of the tissue layers to be joined.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A tissue anchor system including a suture attached to a needle, the system comprising:
 a set of nestable anchors including a first anchor having a first shaft, a second anchor having a second shaft, and a third anchor having a third shaft, wherein the second shaft is insertable into and adapted to nest in the first shaft and the third shaft is insertable into and adapted to nest in the second shaft;
 wherein the first shaft, the second shaft and the third shaft each has an outer surface that tapers from a proximal end to a distal end thereof that is narrower than the proximal end thereof, wherein the distal end of the second shaft is insertable into the proximal end of the first shaft and the distal end of the third shaft is insertable into the proximal end of the second shaft;
 wherein the outer surface of the first shaft, the second shaft and the third shaft each includes a plurality of barbs located distal the proximal end thereof;
 wherein the outer surface of each of the first shaft and the second shaft is smooth with an absence of barbs between the distal end and a shaft mid-point thereof;
 wherein the first shaft, the second shaft and the third shaft each has a lumen extending from the proximal end through the distal end thereof; and
 wherein, during use, the set of nestable anchors is configured such that the second shaft is nested in the first shaft, the third shaft is nested in the second shaft, and is suspended by the suture attached to the needle that is inserted through the lumen of the first shaft, the lumen of the second shaft and the lumen of the third shaft.

2. The tissue anchor system according to claim 1, wherein the plurality of barbs of the outer surface of each of the first shaft and the second shaft includes barbs located between a shaft mid-point and the proximal end.

3. The tissue anchor system according to claim 1, wherein the anchors include one or more polymeric material components.

4. The tissue anchor system according to claim 1, wherein a first opening in the proximal end of each of the first shaft and the second shaft is configured with a first diameter that is larger than a second diameter of a second opening in the distal end of each of the first shaft and the second shaft.

5. The tissue anchor system according to claim 1, wherein each of the plurality of barbs includes a living hinge.

6. The tissue anchor system according to claim 1, wherein the proximal end of the first shaft and the second shaft includes a flange provided around a first opening formed in the proximal end of each of the first shaft and the second shaft.

7. The tissue anchor system according to claim 1, wherein the suture is attached to a trailing end of the needle.

8. The tissue anchor system according to claim 7, further comprising a stopper, the stopper being attached to an opposite end of the suture relative to the needle.

9. A kit of parts for surgical anchor placement including:
a needle having a front end and a trailing end;
a length of suture having a first end attached to the trailing end of the needle and a second end provided with a stopper; and
a plurality of surgical anchors including
a first anchor having a first shaft, a second anchor having a second shaft, and a third anchor having a third shaft, wherein the second shaft is insertable into and adapted to nest in the first shaft and the third shaft is insertable into and adapted to nest in the second shaft;
wherein the first shaft, the second shaft and the third shaft each has an outer surface that tapers from a proximal end to a distal end thereof that is narrower than the proximal end thereof, wherein the distal end of the second shaft is insertable into the proximal end of the first shaft and the distal end of the third shaft is insertable into the proximal end of the second shaft;
wherein the outer surface of the first shaft, the second shaft and the third shaft each includes a plurality of barbs located distal the proximal end thereof;
wherein the outer surface of each of the first shaft and the second shaft is smooth with an absence of barbs between the distal end and a shaft mid-point thereof;
wherein the first shaft, the second shaft and the third shaft each has a lumen extending from the proximal end through the distal end thereof;
wherein, during use, the set of nestable anchors is configured such that the second shaft is nested in the first shaft, the third shaft is nested in the second shaft, and is suspended by the suture attached to the needle that is inserted through the lumen of the first shaft, the lumen of the second shaft and the lumen of the third shaft; and
wherein each of the plurality of surgical anchors is held on the length of suture between the first and the second ends of the suture.

10. The kit of parts as claimed in claim 9, wherein, for both the second shaft and the third shaft, a portion of the shaft between the distal end and the shaft mid-point nests into the lumen of a neighbouring anchor.

11. The kit of parts as claimed in claim 9, wherein, for both the first and second shaft, a proximal opening of the lumen of the shaft is configured to receive the distal end portion of the shaft of another one of the plurality of anchors.

12. The kit of parts as claimed in claim 9, further including a surgical implant.

13. The kit of parts as claimed in claim 12, provided in a packaging and including a set of instructions for use.

14. The kit of parts as claimed in claim 9, provided in a packaging and including a set of instructions for use.

15. A method of preparing a kit of parts for surgical anchor placement, including:
providing a needle having a first end of a length of suture attached to a trailing end of the needle;
providing a stopper at a second end of the length of suture; and
receiving a plurality of surgical anchors on the length of suture between first and second ends of the length of suture by moving the needle and the suture through a through-going lumen of an anchor shaft of each of the plurality of surgical anchors, such that a distal end of the first received surgical anchor abuts the stopper at the second end of the length of suture,
wherein the plurality of surgical anchors includes a first anchor having a first shaft, a second anchor having a second shaft, and a third anchor having a third shaft, wherein the second shaft is insertable into and adapted to nest in the first shaft and the third shaft is insertable into and adapted to nest in the second shaft;
wherein the first shaft, the second shaft and the third shaft each has an outer surface that tapers from a proximal end to a distal end thereof that is narrower than the proximal end thereof, wherein the distal end of the second shaft is insertable into the proximal end of the first shaft and the distal end of the third shaft is insertable into the proximal end of the second shaft;
wherein the outer surface of the first shaft, the second shaft and the third shaft each includes a plurality of barbs located distal the proximal end thereof;
wherein the outer surface of each of the first shaft and the second shaft is smooth with an absence of barbs between the distal end and a shaft mid-point thereof;
wherein the first shaft, the second shaft and the third shaft each has a lumen extending from the proximal end through the distal end thereof;
wherein, during use, the set of nestable anchors is configured such that the second shaft is nested in the first shaft, the third shaft is nested in the second shaft, and is suspended by the suture attached to the needle that is inserted through the lumen of the first shaft, the lumen of the second shaft and the lumen of the third shaft.

16. The method according to claim 15, further including:
providing a set of instructions for use;
providing a packaging; and
arranging the needle with the plurality of surgical anchors received on the length of suture and the set of instructions for use in the packaging.

17. The method according to claim 16, wherein the needle and the plurality of surgical anchors received on the length of suture is sterilized prior to use.

* * * * *